(12) United States Patent
Pokrajac

(10) Patent No.: US 8,994,537 B2
(45) Date of Patent: Mar. 31, 2015

(54) HAND SANITIZER COMPLIANCE DETECTION SYSTEM

(75) Inventor: Dalibor Pokrajac, Coquitlam (CA)

(73) Assignee: Guard RFID Solutions Inc., Delta BC (CA)

( * ) Notice: Subject to any disclaimer, the term of this patent is extended or adjusted under 35 U.S.C. 154(b) by 121 days.

(21) Appl. No.: 13/552,493

(22) Filed: Jul. 18, 2012

(65) Prior Publication Data

US 2013/0187779 A1    Jul. 25, 2013

Related U.S. Application Data

(60) Provisional application No. 61/509,141, filed on Jul. 19, 2011.

(51) Int. Cl.
| | |
|---|---|
| G08B 23/00 | (2006.01) |
| G08B 21/18 | (2006.01) |
| G06F 19/00 | (2011.01) |
| G08B 21/24 | (2006.01) |

(52) U.S. Cl.
CPC .............. *G08B 21/18* (2013.01); *G06F 19/327* (2013.01); *G08B 21/245* (2013.01)
USPC ...................... 340/573.1; 340/286.07; 222/23

(58) Field of Classification Search
CPC ............................ G08B 21/245; G06F 19/327
USPC .............. 340/573.1, 539.11, 539.12, 286.07; 222/23
See application file for complete search history.

(56) References Cited

U.S. PATENT DOCUMENTS

| | | | |
|---|---|---|---|
| 7,898,407 B2* | 3/2011 | Hufton et al. .............. | 340/573.1 |
| 8,237,558 B2* | 8/2012 | Seyed Momen et al. ........................ | 340/539.11 |
| 2012/0112914 A1* | 5/2012 | Wegelin et al. ............ | 340/573.1 |
| 2012/0218106 A1* | 8/2012 | Zaima et al. .................. | 340/540 |
| 2013/0033376 A1* | 2/2013 | Seyed Momen et al. ........................ | 340/539.11 |
| 2014/0015670 A1* | 1/2014 | Wegelin et al. ............ | 340/539.1 |

* cited by examiner

*Primary Examiner* — John A Tweel, Jr.

(57) ABSTRACT

A hand sanitizer compliance detection system for RFID-tagged employees comprises a hand sanitizer station with a detector enclosure having a sensor and an aperture that narrows a field of view by the sensor to define a hand detection zone.

20 Claims, 7 Drawing Sheets

Fig. 2a
Fig. 2b
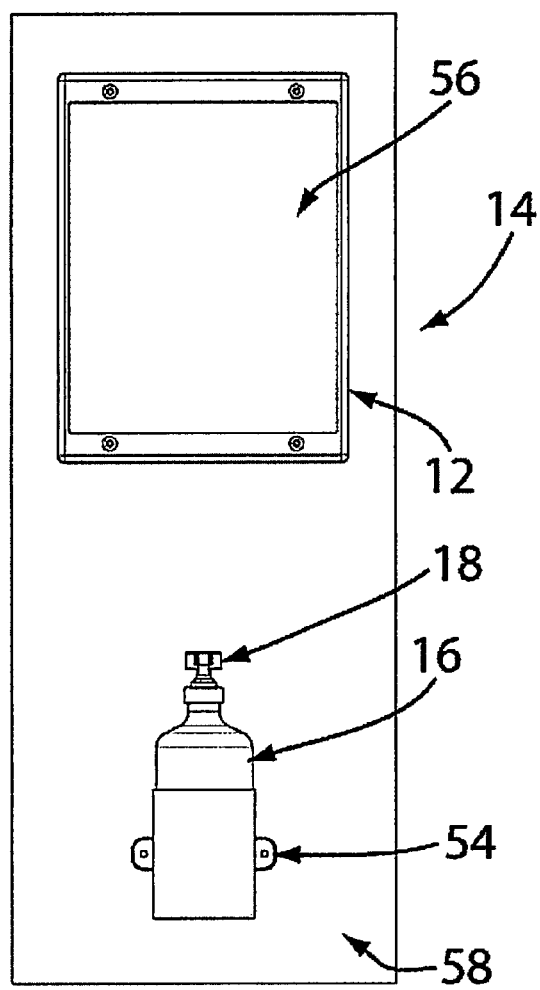
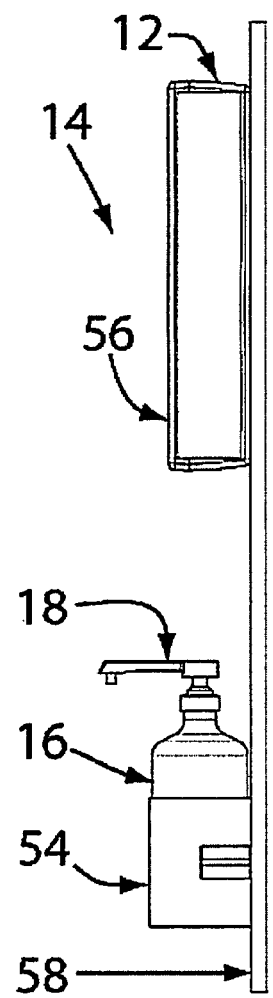

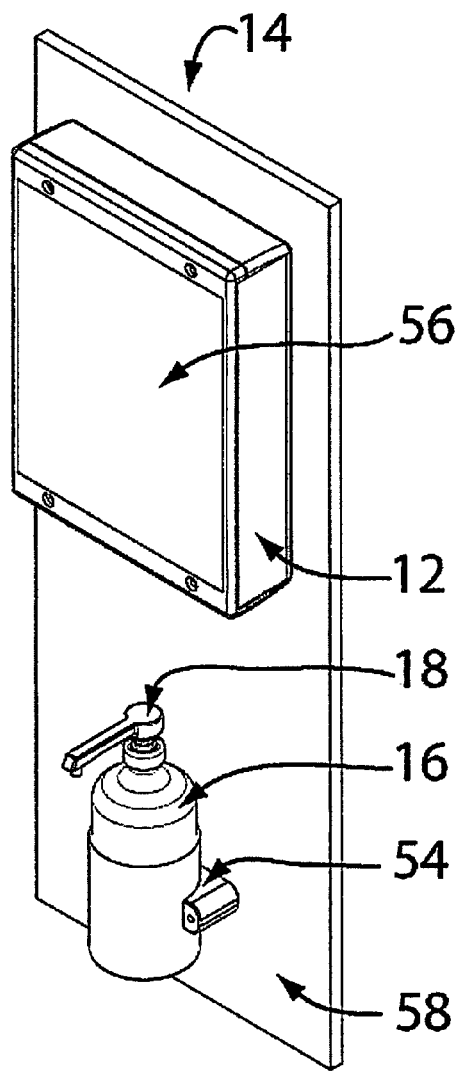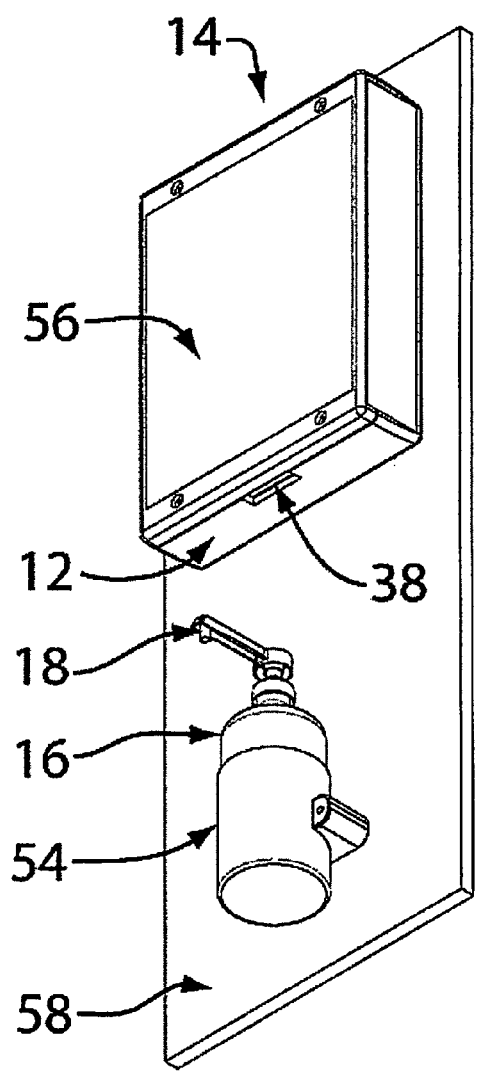

Fig. 3a
Fig. 3b
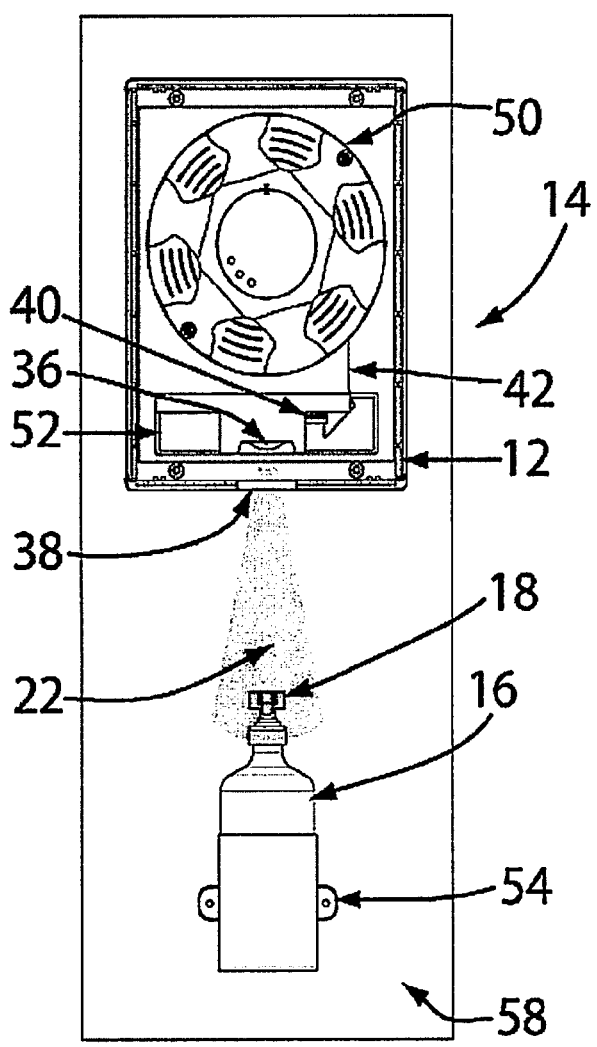
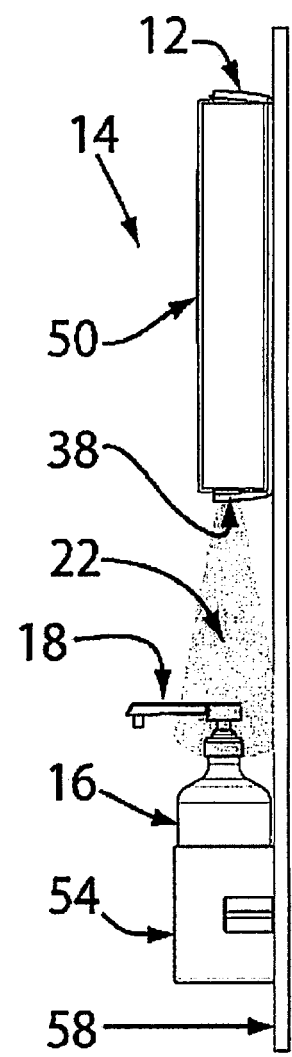

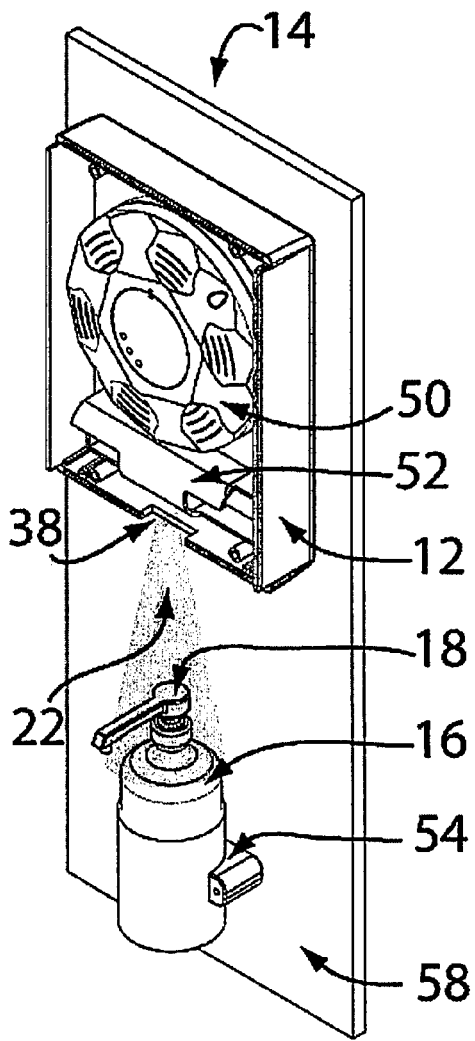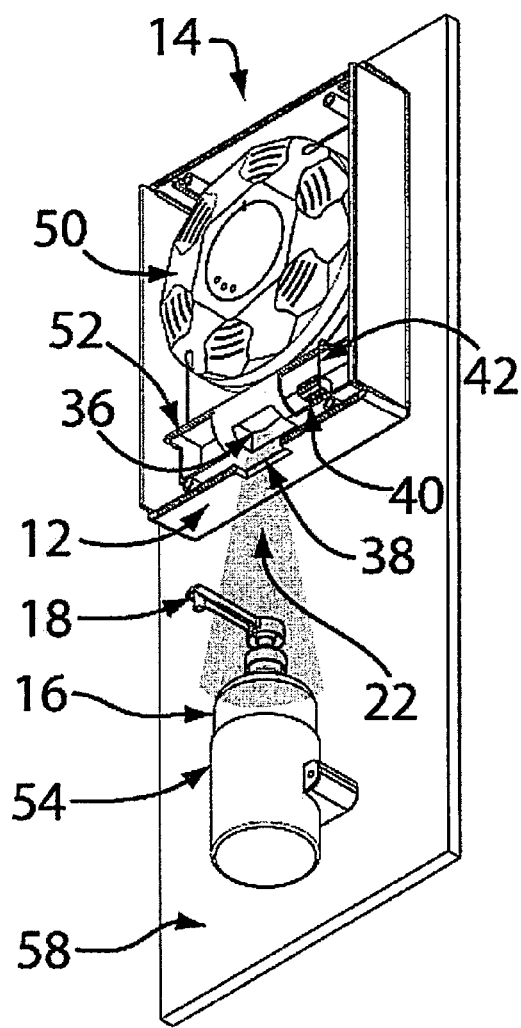

HAND SANITIZER COMPLIANCE DETECTION SYSTEM

FIELD OF INVENTION

This invention relates to a novel device in the general field of hand sanitizer compliance systems that utilize radio frequency identification (RFID) technology, and more specifically to a hand sanitizer compliance detection system that eliminates false RFID activations from bystanders, thereby ensuring accurate and thorough compliance monitoring.

BACKGROUND OF THE INVENTION

Health care and food service employers are required to ensure consistent hand hygiene of their employees. Compliance systems for hand hygiene that utilize RFID technology have existed at least since 2007. These systems often send a signal to an employee's RFID badge or tag that records their presence at, or use of a hand sanitizer station. Unfortunately these systems can also create false or misleading activations due to the proximity of other RFID tagged employees while the station is being used, or by tagged employees inadvertently triggering the compliance detector while passing nearby an unused station. Therefore, a hygiene compliance system is needed that ensures only data from the employee who is actually using the station is recorded and transmitted to the monitoring organization.

BRIEF SUMMARY OF THE INVENTION

The disclosed hand sanitizer compliance detection system is designed to provide a means to detect hand sanitation by RFID tagged employees so that this activity can be reliably and accurately monitored. The compliance system detector narrows the field of detection to indicate actual use of the hand sanitizer as opposed to mere proximity to the sanitizer station. This avoids the situation where the RFID system detects one or more users due to their proximity to the station even if they are not using the station. Given the health and legal liabilities of inadequate hand hygiene in the healthcare or foodservice industries, accurate compliance monitoring is improved when use of the sanitizer is linked with the user's RFID as logged by the system.

The present implementation can also be employed within any condition responsive indicating system where a physical interaction can be connected with an individual's RFID and logged in the monitoring system. Examples can include, but are not limited to entry access control and monitoring, safety activation controls, emergency equipment access, shipboard station-keeping, fire alarm activation & location monitoring.

DRAWINGS

Brief Description of the Drawings

FIG. 2a shows a front view of a hand sanitation compliance detection station when not in use. FIG. 2b shows a side view of a station when not in use. FIG. 2c shows a top isometric view of an unused station, while FIG. 2d shows an isometric view of an unused station from below.

FIG. 3a shows a front view of a hand sanitation compliance detection station with the detector's enclosure coverplate removed and the detection zone highlighted. FIG. 3b shows a side view of FIG. 3a, while FIG. 3c shows a top isometric view and FIG. 3d a bottom isometric view of same.

DETAILED DESCRIPTION

All elements will now be introduced by reference to figures. The function of each element and its interaction with other elements will also be described where necessary.

Figure 1:
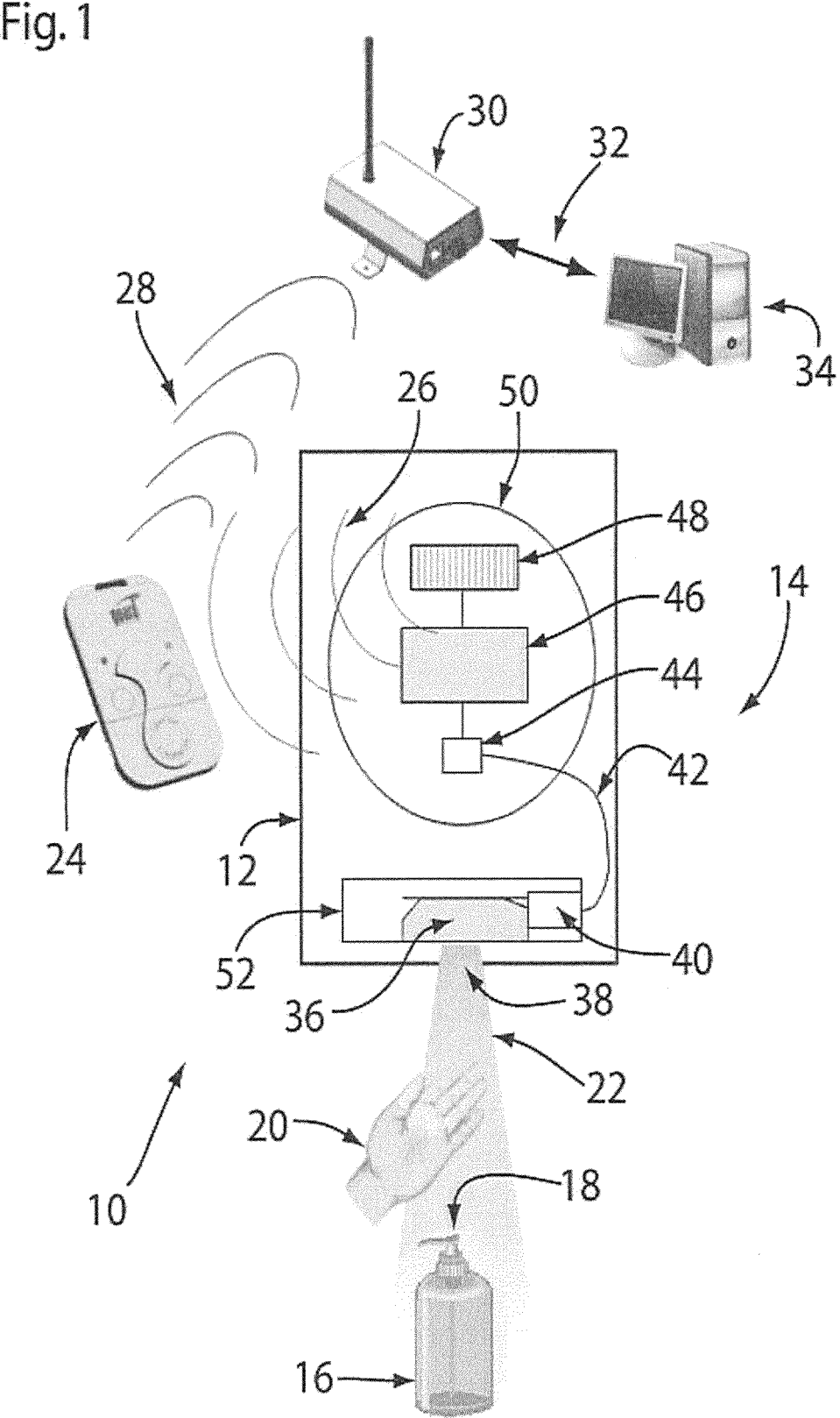
FIG. 1 shows a diagram illustrating the basic elements and operation of the Hand Sanitizer Compliance Detection System.

FIG. 1 diagrams the basic elements and operation of the Hand Sanitizer Compliance Detection System 10. A hand 20 is inserted into the detection zone 22 of a station 14, above the dispenser 18 of a sanitizer bottle 16, and is detected by a sensor 36 through an aperture 38 of a detector enclosure 12. The sensor enclosure 52 also houses a dry contact 40 which sends the output of the sensor 36 to the generator input 44 by means of a wired connection 42 which then activates a signal generator 46 which transmits a detector signal 26 by means of an antenna/transmitter 48 to the user's RFID tag 24. This tag 24 then transmits an RFID signal 28 to the network's RFID tag reader 30 which relays user compliance data 32 to the monitoring server 34.

FIG. 2a shows a front view of a hand sanitation compliance detection station 14 as it is seen by the user, with a coverplate 56 affixed to the detector enclosure 12 which is then affixed to a wallboard 58 for mounting on a wall or other surface. Also affixed to the station 14 wallboard 58 is a sanitizer bottle 18 with its dispenser 18 (plunger & dispensing nozzle) shown within its bottle holder 54 & attachment assembly. FIGS. 2b, 2c & 2d show side, top isometric and below isometric views of the same elements shown in FIG. 2a with the exception of FIG. 2d, wherein the aperture 38 of the detector enclosure 12 is visible from underneath.

FIG. 3a shows a front view of a hand sanitation compliance detection station 14 with the detector's enclosure 12 coverplate 56 removed and the detection zone 22 highlighted by the shaded area above the dispenser 18 of the bottle 16 in its holder 54. The detection zone 22 begins at the sensor 36 which views a narrow field around the dispenser 18 through the aperture 38 of the detector enclosure 12. The sensor 36 is housed within the sensor enclosure 52, along with a dry contact 40 which routes sensor 36 detections into the generator enclosure 50 by means of a wired connection 42. FIG. 3b shows a side view the same elements found in FIG. 3a, while FIG. 3c shows a top isometric view and FIG. 3d a bottom isometric view of same.

Figure 4:
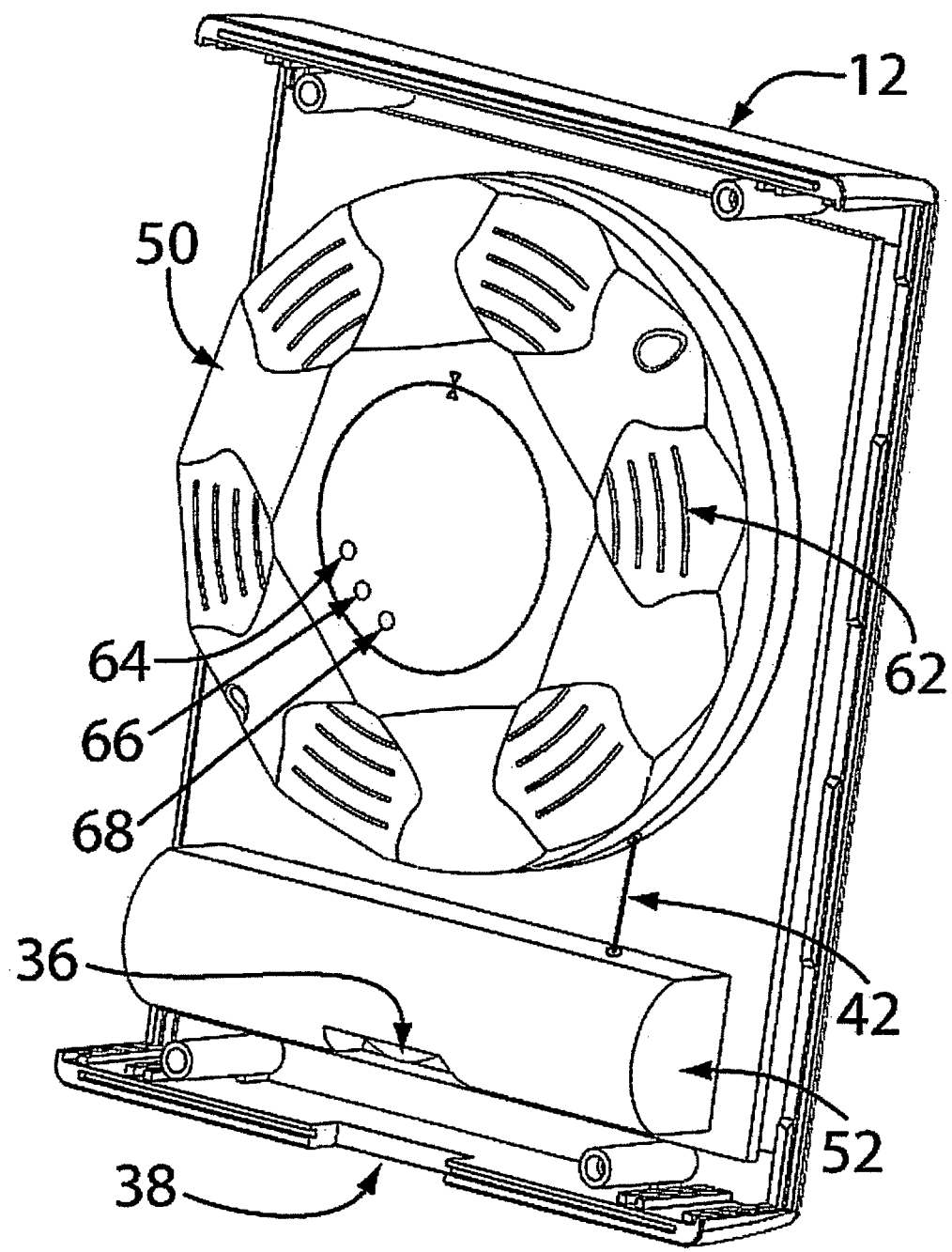
FIG. 4 shows a closeup of the elements inside a detector enclosure.

FIG. 4 shows a closeup of some of the elements inside a detector enclosure 12, including the generator enclosure 50 with its vents 62, and its power 64, network 66 and error 68 LED indicators. Vents 62 allow heat generated by electronics inside the enclosure 50 to escape. The power LED 64 indicates that electronics are turned on; the network LED 66 indicates that the LF/IR generator 46 is connected to the RFID network; and the error LED 68 is able to indicate various error conditions by its flash rate & duration. Also shown is the sensor enclosure 52 with its sensor 36 monitoring the dispenser 18 (see FIGS. 3c/d) through the aperture 38, and its connection 42 into the generator enclosure 50. The circular shape of the generator enclosure 50 allows vents 62 to be evenly distributed around the internal signal (and heat) generating electronics and also provides aesthetic qualities not inherent with a square enclosure.

Figure 5:
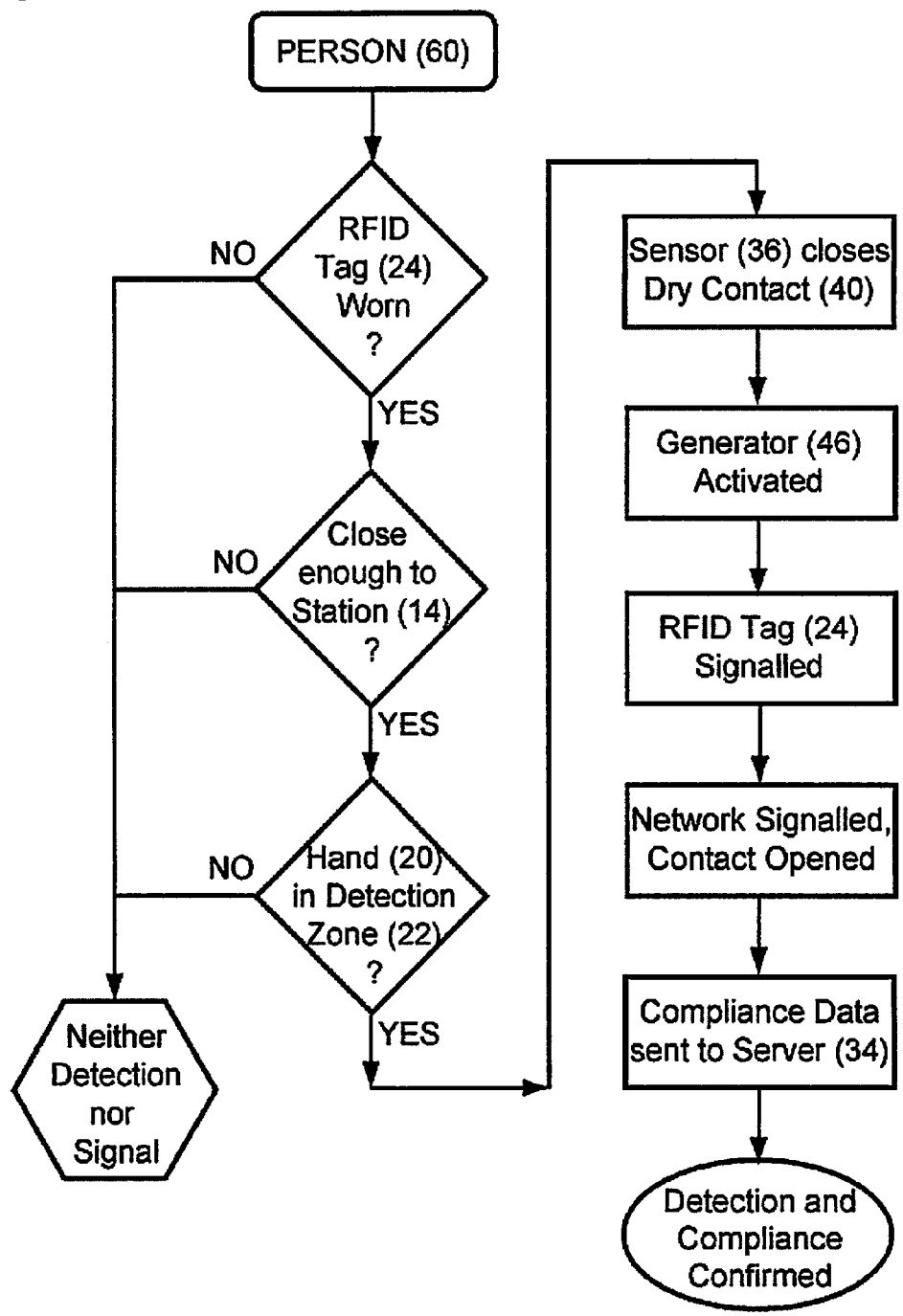
FIG. 5 shows a flowchart detailing the operational protocol of the Hand Sanitizer Compliance Detection System.

FIG. 5 shows a flowchart detailing the operational decision protocol of the Hand Sanitizer Compliance Detection System which will be explained in more detail below. A person 60 wearing an RFID tag 24 must both be close enough to the station 14 and have their hand 20 within the narrow field of the detection zone 22 in order for their action to be detected and compliance communicated to the server 34.

The preferred embodiment of the hand sanitizer compliance detection system will now be described.

RFID monitoring systems usually operate within a large area or field of detection, but when employed as a condition responsive indicating system this broad field of application can cause false detections. Problem: An RFID tagged person walks near enough to the RFID detector that he is inadvertently logged by the system as sanitizing hands due to his proximity to the RFID detector, when actually the sanitizer is not in use. Such false detection can occur due to the continuous operation of Tag Exciter inside HSS which activates all related RFID Tags on people passing by. The intention of this invention is to activate HSS (and consequently read RFID Tag) only when a person is actually using sanitizer. Solution: a narrow field infrared sensor detects presence of hands 20 within a detection zone 22 above the hand sanitation dispenser 18, and only then enables activation of low frequency RF field (near field or magnetic) or infrared field which activates the RFID Tag 24 and enables accurate RFID communication of hygiene compliance to the monitoring agency. RFID compliance activation dependent on IR hand detection within a narrow field zone (see FIGS. 3a-d) prevents false detection and creates accurate hygiene compliance monitoring and reporting.

FIGS. 3a-d show a detection zone 22 with the very narrow detection angle required in order to prevent false triggering by RFID tagged 24 people 60 adjacent to the station 14 while it is not being used. An appropriately narrow detection angle may be achieved by limiting the field of view of the sensor 36 by use of a focusing lens and/or limiting the size of the sensor's 36 aperture 38 through the detector enclosure 12. In the preferred embodiment the size and the shape of the aperture 38 in the detector enclosure 12 is critical to control the size of IR sensor 36 detection zone 22, and therefore to prevent sensor 36 activation by non station 14 using bystanders.

In combination with FIG. 1, the flowchart in FIG. 5 will now be discussed in order to show how RFID activation dependent on narrow IR field detection can produce optimal compliance monitoring and reporting. FIG. 1 shows a hand 20 placed within the detection zone 22 of an IR sensor 36, the field of which has been narrowed to cover only the region of the dispenser 18 of hand sanitizing bottle 16. Referring to FIG. 5, if that person 60 is wearing an RFID tag 24, then they meet all the conditions necessary to both detect and signal hand sanitizer use compliance. As shown in both FIGS. 1 & 5, the following steps then take place, namely the dry contact 40 is closed when the user's hand 20 is detected in the IR sensor 36 detection zone 22; a wired connection 42 between the closed dry contact 40 and the generator input 44 activates the LF or IR generator 46; a detection signal 26 is emitted from the generator 46 by means of the antenna/transmitter 48; after the hand 20 is removed, the dry contact 40 is opened and the generator 46 is de-activated automatically; upon receiving the LF or IR detector signal 26 from the LF or IR generator 46, the RFID tag 24 transmits a UHF signal 28 to a networked RFID tag reader 30; the transmitted signal 28 carries LF or IR field ID (transmitted by generator 46) and its own ID; data 32 from networked tag readers 24 are then collected and evaluated at a central server 34 for hygiene compliance and recordkeeping.

Other embodiments are not ruled out or similar methods leading to the same result. The foregoing description of the preferred apparatus and method of installation should be considered as illustrative only, and not limiting. Other forming techniques, circuitry, and other materials may be employed towards similar ends. Various changes and modifications will occur to those skilled in the art, without departing from the true scope of the invention as defined in the above disclosure, and the following claims.

I claim:

1. A hand sanitizer compliance detection system for RFID-tagged employees, comprising a hand sanitizer station with a detector enclosure having a sensor and an aperture that narrows a field of view by the sensor to define a hand detection zone, in which an enclosure for the sensor houses means for sending output of the sensor to a signal generator input by a wired connection, which activates a signal generator which transmits a detector signal by an antenna to a user's RFID tag.

2. The hand sanitizer compliance detection system of claim 1, in which the sensor views a narrowed field around a hand sanitizer dispenser through the aperture of the detector enclosure.

3. The hand sanitizer compliance detection system of claim 2, further comprising an RFID tag for a user of the system, in which the sensor detects use of the hand sanitizer dispenser by the user.

4. The hand sanitizer compliance detection system of claim 3, in which the system logs usage of the hand sanitizer dispenser by the user.

5. The hand sanitizer compliance detection system of claim 1, in which a user detection zone is defined by the aperture in combination with the sensor and is located above a sanitizer dispenser.

6. The hand sanitizer compliance detection system of claim 1, in which an enclosure for the sensor houses a dry contact which sends output of the sensor to a signal generator input by a wired connection, which activates a signal generator which transmits a detector signal by an antenna to a user's RFID tag.

7. The hand sanitizer compliance detection system of claim 6, in which the RFID tag transmits an RFID signal to an RFID network tag reader which relays user compliance data to a monitoring server.

8. The hand sanitizer compliance detection system of claim 2, in which the hand sanitizer dispenser comprises a sanitizer container, a plunger, and a dispensing nozzle.

9. The hand sanitizer compliance detection system of claim 6, in which the detector enclosure includes a generator enclosure for the signal generator, the generator enclosure having vents.

10. The hand sanitizer compliance detection system of claim 9, further comprising power, network, and error LED indicators.

11. The hand sanitizer compliance detection system of claim 9, in which the generator enclosure has a circular shape and the vents are evenly distributed around internal signal generating electronics.

12. The hand sanitizer compliance detection system of claim 1, in which a user wearing an RFID tag in proximity to the hand sanitizer station and having a hand within the detection zone causes hand sanitizer compliance to be communicated to a server.

13. The hand sanitizer compliance detection system of claim 1, in which the sensor is a narrow field infrared sensor capable of detecting a presence of a user's hands within the detection zone.

14. The hand sanitizer compliance detection system of claim 13, in which the sensor only upon detecting the presence of the user's hands within the detection zone enables activation of a field which activates an RFID tag worn by user and enables RFID communication of sanitizer usage compliance to a monitoring system.

15. The hand sanitizer compliance detection system of claim 1, in which a focusing lens for the sensor in combination with an appropriate size and shape of the aperture is used to achieve an appropriately narrow detection angle for the sensor.

16. The hand sanitizer compliance detection system of claim 6, in which after a user's hand is removed from the detection zone, the dry contact is opened and the signal generator is de-activated automatically.

17. The hand sanitizer compliance detection system of claim 1, in which data from networked RFID tag readers is collected and evaluated at a central server for hygiene compliance and recordkeeping.

18. The hand sanitizer compliance detection system of claim 4, in which: a) a user detection zone is defined by the aperture in combination with the sensor and is located above a sanitizer dispenser; b) an enclosure for the sensor houses a dry contact which sends output of the sensor to a signal generator input by a wired connection, which activates a signal generator which transmits a detector signal by an antenna to a user's RFID tag; c) the sensor is a narrow field infrared sensor capable of detecting a presence of a user's hands within the detection zone; d) the sensor only upon detecting the presence of the user's hands within the detection zone enables activation of a signal generator field which activates an RFID tag worn by user and enables RFID communication of sanitizer usage compliance to a monitoring system; e) a user wearing an RFID tag in proximity to the hand sanitizer station and having a hand within the detection zone of the sensor causes hand sanitizer compliance to be communicated to a server, f) after a user's hand is removed from the detection zone, the dry contact is opened and the signal generator is de-activated automatically, g) the RFID tag transmits an RFID signal to an RFID network tag reader which relays user compliance data to a monitoring server.

19. The hand sanitizer compliance detection system of claim 18, in which data from networked RFID tag readers is collected and evaluated at a central server for hygiene compliance and recordkeeping.

20. The hand sanitizer compliance detection system of claim 18, in which: a) the detector enclosure includes a generator enclosure for the signal generator, the generator enclosure having vents and having power, network, and error LED indicators; b) the generator enclosure has a circular shape and the vents are evenly distributed around internal signal generating electronics.

* * * * *